(12) United States Patent
Gleave et al.

(10) Patent No.: US 8,710,020 B2
(45) Date of Patent: Apr. 29, 2014

(54) CLUSTERIN ANTISENSE THERAPY FOR TREATMENT OF CANCER

(75) Inventors: Martin E. Gleave, Vancouver (CA); Scott D. Cormack, Richmond (CA)

(73) Assignee: The University of British Columbia, Vancouver (CA)

( * ) Notice: Subject to any disclaimer, the term of this patent is extended or adjusted under 35 U.S.C. 154(b) by 1673 days.

(21) Appl. No.: 11/470,331

(22) PCT Filed: Apr. 4, 2005

(86) PCT No.: PCT/CA2005/000531
§ 371 (c)(1),
(2), (4) Date: Sep. 6, 2006

(87) PCT Pub. No.: WO2005/094899
PCT Pub. Date: Oct. 13, 2005

(65) Prior Publication Data
US 2008/0119425 A1    May 22, 2008

Related U.S. Application Data

(60) Provisional application No. 60/559,324, filed on Apr. 2, 2004, provisional application No. 60/649,327, filed on Feb. 2, 2005.

(51) Int. Cl.
*C12N 15/11* (2006.01)
(52) U.S. Cl.
USPC ........................................................ 514/44 A
(58) Field of Classification Search
USPC ........................................................ 514/44 A
See application file for complete search history.

(56) References Cited

U.S. PATENT DOCUMENTS

| 5,417,978 A | 5/1995 | Tari et al. |
| 5,563,255 A | 10/1996 | Monia et al. |
| 5,646,042 A | 7/1997 | Stinchcomb et al. |
| 5,789,389 A | 8/1998 | Tarasewicz et al. |
| 5,801,154 A | 9/1998 | Baracchini et al. |
| 5,855,911 A | 1/1999 | Lopez-Berestein et al. |
| 5,877,309 A | 3/1999 | McKay et al. |
| 5,929,040 A | 7/1999 | Werther et al. |

(Continued)

FOREIGN PATENT DOCUMENTS

| WO | WO99/51259 | 10/1999 |
| WO | WO 00/34469 | 6/2000 |

(Continued)

OTHER PUBLICATIONS

Agrawal et al., Antisense Therapeutics: is it as simple as complementary base recognition, Molecular Medicine Today, 2000, pp. 72-81, vol. 6, Publisher: Elsevier Science Ltd.

(Continued)

*Primary Examiner* — Jon E Angell
(74) *Attorney, Agent, or Firm* — John P. White; Gary J. Gershik; Cooper & Dunham LLP

(57) ABSTRACT

A method for providing antisense therapy which reduces the expression of clusterin to provide therapeutic benefits in the treatment of cancer comprising administering from 40 to 640 mg anti-clusterin antisense oligonucleotide to a patient in need of treatment for a cancer expressing clusterin is provided. The method may include administering chemotherapeutic agent or agents, radiotherapy, and/or hormone ablation therapy. The invention also encompasses pharmaceutical compositions formulated to provide a dosage of 40 to 640 mg, and use of antisense in formulating a medicament.

32 Claims, 8 Drawing Sheets

Tissue PK Analysis of OGX-011 in Prostate Tissue

(56) References Cited

U.S. PATENT DOCUMENTS

| | | | |
|---|---|---|---|
| 5,945,290 | A | 8/1999 | Cowsert et al. |
| 5,998,148 | A | 12/1999 | Bennett et al. |
| 6,111,094 | A | 8/2000 | Bennett et al. |
| 6,172,216 | B1 | 1/2001 | Bennett et al. |
| 6,335,194 | B1 | 1/2002 | Bennett et al. |
| 6,383,808 | B1 | 5/2002 | Monia et al. |
| 6,451,991 | B1 | 9/2002 | Martin et al. |
| 6,900,187 | B2 | 5/2005 | Gleave et al. |
| 7,285,541 | B2 | 10/2007 | Gleave et al. |
| 7,368,436 | B2 | 5/2008 | Gleave et al. |
| 7,534,773 | B1 | 5/2009 | Gleave et al. |
| 7,569,551 | B2 | 8/2009 | Gleave et al. |
| 7,592,323 | B1 | 9/2009 | Gleave et al. |
| 7,732,422 | B2 | 6/2010 | Gleave et al. |
| 2002/0128220 | A1 | 9/2002 | Gleave |
| 2003/0105051 | A1 | 6/2003 | McSwiggen |
| 2003/0158130 | A1 | 8/2003 | Gleave et al. |
| 2003/0158143 | A1 | 8/2003 | Gleave et al. |
| 2004/0053874 | A1 | 3/2004 | Monia et al. |
| 2004/0096882 | A1 | 5/2004 | Gleave et al. |
| 2004/0220131 | A1 | 11/2004 | Jackson et al. |
| 2004/0224914 | A1 | 11/2004 | Jackson et al. |
| 2008/0014198 | A1 | 1/2008 | Gleave et al. |
| 2009/0258089 | A1 | 10/2009 | Gleave et al. |

FOREIGN PATENT DOCUMENTS

| | | |
|---|---|---|
| WO | WO 00/49937 | 8/2000 |
| WO | WO 01/46455 | 6/2001 |
| WO | WO 02/22635 | 3/2002 |
| WO | WO 03/062421 | 7/2003 |
| WO | WO 03/072591 | 9/2003 |
| WO | WO 2004/018675 | 3/2004 |
| WO | WO 2004/018676 | 3/2004 |

OTHER PUBLICATIONS

Aoki et al, RNA interference may be more potent than antisense RNA in human cancer cell lines, Clinical and Experimental Pharmacology and Physiology, 2003, pp. 96-102.

Benner et al, Combination of Antisense Oligonucleotide and Low-Dose Chemotherapy in Hematological Malignancies, Journal of Pharmacologoical and Toxicological Methods, 1997, pp. 229-235, Publisher: Elsevier Science Inc.

Boral et al., Clinical evaluation of biologically targeted drugs: obstacles and opportunities, Cancer Chemother Pharmacol, 1998, pp. S3-S21, vol. 42 Suppl, Publisher: Springer-Verlag.

Branch, A good antisense molecule is hard to find, TIBS, 1998, pp. 45-50, Publisher: Elsevier Science Ltd.

Brem, Angiogenesis and cancer control: from concept to therapeutic trial, Cancer Control Journal, 1999, vol. 6, No. 5, Publisher: H. Lee Moffitt Cancer Center & Research Institute.

Bruchovsky et al., Control of tumor progression by maintenance of apoptosis, www.prostatepointer.org ,1996, Publisher: Wiley-Liss, Inc.

Buttyan et al. Induction of the TRPM-2 gene in cells undergoing programmed death, Molecular and Cellular Biology, 1989, pp. 3473-3481, vol. 9, No. 8, Publisher: American Society for Microbiology.

Cox et al., Angiogenesis and non-small cell lung cancer, Lung Cancer, 2000, pp. 81-100, Publisher: Elsevier Science Ltd.

Crooke, Basic principles of antisense therapeutics, Antisense Research and Application, 1998, pp. 150, Chapter 1, Publisher: Springer-Verlag.

Crooke, Progress in antisense technology, Annu Rev Med, 2004, vol. 55, pp. 61-95.

U.S. Appl. No. 12/886,027, filed Sep. 20, 2010, Gleave et al.

U.S. Appl. No. 12/753,995, filed Apr. 5, 2010, Gleave et al.

Agrawal, Importance of nucleotide sequence and chemical modifications of antisense oligonucleotides. 1999, Biochimica et Biophysica Acta, 53-68.

Biroccio et al., The future of antisense therapy: combination with anticancer treatments. Ongogene, 2003; vol. 22, 6579-6588.

Carthew et al., Gene silencing by double-stranded RNA. Current Opinions in Cell Biology, 2001; vol. 13, 244-248.

Elbashir et al., Duplexes of 21-nucleotide RNAs mediate RNA interference in cultured mammalian cells. Nature, 2001; vol. 411, 494-498.

Fieden et al., Expanding the design horizon of antisense oligonucleotides with alpha-L-LNA. Nucleic Acids Research, 2003, vol. 31, No. 21 6365-6372.

Fire et al., Potent and specific genetic interference by double-stranded RNA in Caenorhabdis elegans. Nature, 1998; vol. 391, 806-811.

Horoszewitcz et al., LNCaP Model of Human Prostatic Carcinoma. Cancer Research, Apr. 1983; 43:1809-1818.

Jansen et al., Antisense therapy for cancer-the time of truth. The Lancet Oncology, Nov. 2002; vol. 3 672-683.

Manoharan, 2'-Carbohydrate modifications in antisense oligonucleotide therapy: importance of conformation, configuration, and conjugation. Biochimica et Biophysica Acta 1489 (1999) 117-130.

Metelev et al., Study of Antisense Oligonucleotide Phosphorothioates Containing Segments of Oligodeoxynucleotides and 2'-O-Methylogoribonucleotides. Bioorganic & Medicinal Chemistry Letters, 1994, vol. 4, No. 2 2929-2934.

Miyake et al., Antisense oligodeoxynucleotide therapy targeting clusterin gene for prostate cancer: Vancouver experience from discovery to clinic. International Journal of Urology, Sep. 2005; vol. 12 No. 9 785-794.

Saijo et al., Pharmokinetics, Tissue Distribution, and Stability of Antisense Oligodeoxynucleotide Phosphorothioate., ISIS 3466 in Mice. Oncology Research, 1994; Vo. 6 No. 6, 243-249 (Abstract and Introduction Only).

Sledge, Jr. et al., Comparison of chemotherapy with chemohormonal therapy as first-line therapy for metastatic, hormone sensitive breast cancer: An eastern cooperative oncology group study. Journal of Clinical Oncology, 2000; vol. 18, 262-266.

Telford et al., Comparative evaluation of several DNA binding dyes in the detection of apoptosis-associated chromatin degradation by flow cytometry. Cytometry, 1992; vol. 13, 137-143.

Darby et al, Vascular expression of clusterin in experimental cyclosporine nephrotoxicity, Exp Nephrol, 1995, pp. 234-239, Publisher: S. Karger AG.

Diemer et al., Expression of porcine complement cytolysis inhibitor mRNA in cultured aortic smooth muscle cells, The Journal of Biological Chemistry, 1992, pp. 5257-5264, vol. 207, No. 8, Publisher: The American Society for Biochemistry and Molecular Biology, Inc. EMBL accession No. M63376, Jul. 1991.

Genta, New data reaffirm Genta's molecular target as critical factor for enhancing anticancer treatment, www.genta.com , 2001.

Gewirtz, A critical evaluation of the mechanisms of action proposed for the antitumor effects of the anthracycline antibiotics adriamycin and daunorubicin, Biochemical Pharmacology, 1999, pp. 727-741, vol. 57, Publisher: Elsevier Science Inc.

Gleave et al., Use of antisense oligonucleotides targeting the antiapoptotic gene, clusterin/testosterone-repressed prostate message 2, to enhance androgen sensitivity and chemosensitivity in prostate cancer, Urology, 2001, pp. 39-49, vol. 58.

Gleave et al., Targeting anti-apoptotic genes upregulated by androgen withdrawal using antisense oligonucleotides to enhance androgen-and chemo-sensitivity in prostate cancer, Investigational New Drugs, 2002, pp. 145-158, vol. 20.

Gleave et al., Antisense therapy: current status in prostate cancer and other malignancies, Cancer and Metastasis Reviews, 2002, pp. 79-92, vol. 21.

Gleave et al., Antisense targets to enhance hormone and cytotoxic therapies in advanced prostate cancer, Current Drug Targets, 2003, pp. 209-221, vol. 4.

(56) References Cited

OTHER PUBLICATIONS

Green et al., Antisense oligonucleotides: an evolving technology for the modulation of gene expression in human disease, J Am Cell Surg, Jul. 2000, pp. 93-105, vol. 191, No. 1.
Jen et al. Suppression of gene expression by targeted disruption of messenger RNA: available options and current strategies, Stem Cells, 2000, pp. 307-319, vol. 18.
Jones et al., Molecules in focus: clusterin, The International Journal of Biochemistry & Cell Biology, 2002 pp. 427-431, vol. 34.
Kadomatsu et al., Expression of sulfated glycoprotein 2 is associated with carcinogenesis induced by N-nitroso-N-methylurea in rat prostate . . . , Cancer Res, Apr. 1, 1993, pp. 1480-1483, vol. 53, No. 7.
Kirby et al., Bartonella-associated endothelial proliferation depends on inhibition of apoptosis, PNAS, Apr. 2, 2002, pp. 4656-4661, vol. 99, No. 7.
Kunkel et al., Inhibition of glioma angiogenesis and growth in vivo by systemic treatment with a monoclonal antibody against vascular endothelial growth factor receptor-2, Cancer Research, Sep. 15, 2001, pp. 6624-6628, vol. 61.
Kyprianou et al., bcl-2 over-expression delays radiation-induced apoptosis without affecting the cionogenic survival of human prostate, International Journal of Cancer, Jan. 27, 1997, pp. 341-348, vol. 70, No. 3.
Lee et al, in vitro models of prostate apoptosis: clusterin as an antiapoptotic mediator, The Prostate Supplement, 2000, pp. 21-24, vol. 9, Publisher: Wiley-Liss, Inc.
Millar et al., Localization of mRNAs by in-situ hybridization to the residual body at stages IX-X of the cycle of the rat seminiferous, International Journal of Andrology, 1994, pp. 149-160, vol. 17.
Millis et al., Clusterin regulates vascular smooth muscle cell nodule formation and migration, Journal of Cellular Physiology, 2001, pp. 210-219, vol. 186.
Milner et al., Selecting effective antisense reagents on combinatorial oligonucleotide arrays, Nature Biotechnology, 1997, pp. 537-541, vol. 15.
Miyake et al., Antisense TRPM-2 oligodeoxynucleotides chemosensitize human androgen-independent PC-3 prostate cancer cells both in vitro and in vivo, Clinical Cancer Research, May 2000, pp. 1655-1663, vol. 6.
Miyake et al., Testosterone-repressed prostate message-2 is an antiapoptotic gene involved in progression to androgen independence in prostate cancer, Cancer Research, Jan. 1, 2000, pp. 170-176, vol. 60.
Miyake et al., Synergistic chemsensitization and inhibition of tumor growth and metastasis by the antisense oligodeoxynucleotide targeting clusterin gene in a human bladder cancer model, Clinical Cancer Research, Dec. 2001, pp. 4245-4252, vol. 7.
Miyake et al., Novel therapeutic strategy for advanced prostate cancer using antisense oligodeoxynucleotides targeting antiapoptotic genes upregulated after androgen withdrawal to delay androgen-independent progression and enhance chemosensitivity, International Journal of Urology, 2001, pp. 337-349, vol. 8.
Nor et al., Engineering and characterization of functional human microvessels in immunodeficient mice, Laboratory Investigation, Apr. 2001, pp. 453-463, vol. 81, No. 4.
Nor et al., Up-regulation of Bcl-2 in microvascular endothelial cells enhances intratumoral angiogenesis and accelerates tumor growth, Cancer Research, Mar. 1, 2001, pp. 2183-2188, vol. 61.
Opalinska et al., Nucleic-acid therapeutics: basic principles and recent applications, Nature Reviews, Jul. 2002, pp. 503-514, vol. 1.
Raghavan et al., Evolving Strategies of Cytotoxic Chemotherapy for Advanced Prostate Cancer, European Journal of Cancer, 1997, pp. 566-574, vol. 33, No. 4.
Rosenberg et al., Clusterin: physiologic and pathophysiologic considerations, Int. J. Biochem. Cell Biol., 1995, pp. 633-645, vol. 27.
Sensibar et al., Prevention of cell death induced by tumor necrosis factor a in LNCaP cells by overexpression of sulfated glycoprotein-2 (clusterin), Cancer Research, 1995, pp. 2431-2437, vol. 55.
Tran et al., A role for survivin in chemoresistance of endothelial cells mediated by VEGF, PNAS, Apr. 2, 2002, pp. 4349-4354, vol. 99, No. 7.
Trougakos et al., Silencing expression of the clusterin/apolipoprotein j gene in human cancer cells using small interfering RNA induces, Cancer Research, Mar. 1, 2004, pp. 1834-1842, vol. 64.
Vickers et al., Efficient reduction of target RNA's by small interfering RNA and RNase H-dependent antisense agents, The Journal of Biological Chemistry, Feb. 28, 2003, pp. 7103-7118.
Wilson et al., Clusterin is a secreted mammalian chaperone, TIBS, 2000, pp. 95-97, vol. 25.
Wong et al., Molecular characterization of human TRPM-2/clusterin, a gene associated with sperm maturation, apoptosis and neurodegeneration, Eur. J. Biochem, 1994, pp. 917-925, vol. 91.
Wright et al., A ribonucleotide reductase inhibitor, MDL 101,731, induces apoptosis and elevates TRPM-2 mRNA levels in human prostate, Experimental Cell Research, Jan. 10, 1996, pp. 54-60, vol. 222, No. 1.
Yang et al. Nuclear clusterin/XIP8, an x-ray-induced Ku70-binding protein that signals cell death, PNAS, May 23, 2000, pp. 5907-5912, vol. 97, No. 11.
Zellweger et al., Antitumor activity of antisense clusterin oligonudeotides is improved in vitro and in vivo by incorporation of 2'O'(2-methoxy) ethyl chemistry, The Journal of Pharmacology and Experimental Therapeutics, 2001, pp. 934-940, vol. 298, No. 3.
Zellweger et al., Chemosensitization of human renal cell cancer using antisense oligonucleotides targeting the antiapoptotic gene clusterin, Neoplasia, 2001, pp. 360-367.
Zwain et al., Clusterin protects granulosa cells from apoptotic cell death during follicular atresia, Experimental Cell Research, 2000, pp. 101-110, vol. 257.
Zangmeister-Wittke et al., A novel bispecific antisense oligonucleotide inhibiting both bcl-2 and bcl-xL expression efficiently induces apoptosis in tumor cells, Clinical Cancer Research, Jun. 2000, pp. 2547-2555, vol. 6.
Chung et al., Enhanced chemosensitivity of bladder cancer cells to cisplatin by suppression of clusterin in vitro, Cancer Letters, Jan. 2004, pp. 155-161, vol. 203, No. 2.
Dean et al., Antisense oligonucleotide-based therapeutics for cancer, Oncogene, 2003, pp. 9087-9096, vol. 22 No. 56.
Ho et al., Lack of Association between Enhanced TRPM-2/Clusterin Expression and Increased Apoptotic Activity in Sex-Hormone-Induced Prostatic Dysplasia of the Noble Rat, American Journal of Pathology, Jul. 1998, pp. 131-139, vol. 153, No. 1.
Hough et al., Coordinately up-regulated genes in ovarian cancer, Cancer Research, May 15, 2001, pp. 3869-3876, vol. 61, No. 10.
July et al., Clusterin expression is significantly enhanced in prostate cancer cells following androgen withdrawal therapy, The Prostate, 2002, pp. 179-188, vol. 50.
July et al., Nucleotide-based therapies targeting clusterin chemosensitize human lung adenocarcinoma cells both in vitro and in vivo, Molecular Cancer Therapeutics, 2004, pp. 223-232, vol. 3, No. 3.
Miyake et al., Overexpression of clusterin in transitional cell carcinoma of the bladder is related to disease progression and recurrence, Urology, 2002, pp. 150-154, vol. 59, No. 1.
Parker et al., Cancer Statistics, CA Cancer J Clin., Jan./Feb. 1996, pp. 527, vol. 46, No. 1.
Redondo et al., Overexpression of clusterin in human breast carcinoma, American Journal of Pathology, Aug. 2000, pp. 393-399, vol. 157, No. 2.
Schiller et al., Comparison of four chemotherapy regimens for advanced non-small-cell lung cancer, The New England Journal of Medicine, Jan. 10, 2002, pp. 92-98, vol. 346, No. 2.
Zellweger et al., Enhanced radiation sensitivity in prostate cancer by inhibition of the cell survival protein dusterin, Clinical Cancer Research, Oct. 2002, pp. 3276-3284, vol. 8, No. 10.
Bailey et al., Clusterin in the male reproductive system: localization and possible function, Molecular and Cellular Endocrinology, 1999, pp. 17-23, vol. 151.

(56) References Cited

OTHER PUBLICATIONS

Kang et al., Antisense oligonucleotide of clusterin mRNA induces apoptotic cell death and prevents adhesion of rat ASC-17D sertoli cells, Molecules and Cells, Apr. 30, 2000, pp. 193-198, vol. 10, No. 2.

Miyake et al., Acquisition of chemoresistant phenotype by overexpression of the antiapoptotic gene testosterone-repressed prostate message-2 in prostate cancer, Cancer Research, May 1, 2000, pp. 2547-2554, vol. 60.

Moulson et al., Clusterin (apoJ) regulates vascular smooth muscle cell differentiation in vitro, Journal of Cellular Physiology, 1999, pp. 355-364, vol. 180.

Clusterin Levels Increase After Androgen Ablation and During AI Progression

July et al, Prostate 15:179-188, 2002

SEQUENCE LISTING

```
<160> NUMBER OF SEQ ID NOS: 12

<210> SEQ ID NO 1
<211> LENGTH: 21
<212> TYPE: DNA
<213> ORGANISM: human

<400> SEQUENCE: 1
cagcagcaga gtcttcatca t                                          21

<210> SEQ ID NO 2
<211> LENGTH: 21
<212> TYPE: DNA
```

<213> ORGANISM: human

<400> SEQUENCE: 2
attgtctgag accgtctggt c                                        21

<210> SEQ ID NO 3
<211> LENGTH: 21
<212> TYPE: DNA
<213> ORGANISM: human

<400> SEQUENCE: 3
gctgggcgga gttgggggcc t                                        21

<210> SEQ ID NO 4
<211> LENGTH: 21
<212> TYPE: DNA
<213> ORGANISM: human

<400> SEQUENCE: 4
gcacagcagg agaatcttca t                                        21

<210> SEQ ID NO 5
<211> LENGTH: 21
<212> TYPE: DNA
<213> ORGANISM: human

<400> SEQUENCE: 5
gcacagcagc aggatcttca t                                        21

<210> SEQ ID NO 6
<211> LENGTH: 21
<212> TYPE: DNA
<213> ORGANISM: human

<400> SEQUENCE: 6
tggagtcttt gcacgcctcg g                                        21

<210> SEQ ID NO 7
<211> LENGTH: 21
<212> TYPE: DNA
<213> ORGANISM: human

<400> SEQUENCE: 7
ccttcagctt tgtctctgat t                                        21

<210> SEQ ID NO 8
<211> LENGTH: 21
<212> TYPE: DNA
<213> ORGANISM: human

<400> SEQUENCE: 8
agcagggagt cgatgcggtc a                                        21

<210> SEQ ID NO 9
<211> LENGTH: 21
<212> TYPE: DNA
<213> ORGANISM: human

<400> SEQUENCE: 9
atcaagctgc ggacgatgcg g                                        21

<210> SEQ ID NO 10
<211> LENGTH: 21
<212> TYPE: DNA

-continued

```
<213> ORGANISM: human

<400> SEQUENCE: 10
gcaggcagcc cgtggagttg t                                        21

<210> SEQ ID NO 11
<211> LENGTH: 21
<212> TYPE: DNA
<213> ORGANISM: human

<400> SEQUENCE: 11
ttcagctgct ccagcaagga g                                        21

<210> SEQ ID NO 12
<211> LENGTH: 21
<212> TYPE: DNA
<213> ORGANISM: human

<400> SEQUENCE: 12
aatttagggt tcttcctgga g                                        21
```

CLUSTERIN ANTISENSE THERAPY FOR TREATMENT OF CANCER

CROSS REFERENCE TO RELATED APPLICATIONS

This application is related to US Patent Publications 20020128220 and 20030166591 and PCT Publication WO 00/049937, all of which are incorporated herein by reference. This application claims priority from U.S. Provisional Application No. 60/559,324 filed Apr. 2, 2004, and U.S. Provisional Application No. 60/649,326 filed Feb. 2, 2005, which are incorporated herein by reference.

FIELD OF INVENTION

This invention relates to the field of treating cancer, more specifically to the treatment of cancer using an amount of antisense oligodeoxynucleotide effective to result in tumour-appropriate biodistribution and to result in tumour-appropriate biodistribution and to reduce the effective amount of clusterin in cancer cells with limited side effects.

BACKGROUND OF THE INVENTION

Standard treatments for cancer vary depending on type of cancer, stage and location. For local disease, excision and/or radiation may be used. For systemic disease, chemotherapy may be used, and for hormone-dependent tumours, hormone ablation therapy is an option. With the exception of surgery, treatment success is limited by toxicity and resistance.

Research during the past decade has identified several proteins that may promote progression and resistance by inhibiting apoptosis. Of special relevance to development of AI (androgen-independent) progression and hormone refractory prostate cancer (HRPC) are those survival proteins that are up-regulated after apoptotic triggers, such as androgen ablation, that function to inhibit cell death.

Clusterin is a ubiquitous protein with a diverse range of proposed activities. In prostate epithelial cells, expression of clusterin increases immediately following castration, reaching peak levels in rat prostate cells at 3 to 4 days post castration, coincident with the onset of massive cell death. These results have led some researchers to the conclusion that clusterin is a marker for cell death, and a promoter of apoptosis. On the other hand, it has been observed that Sertoli cells and some epithelial cells express high levels of clusterin without increased levels of cell death. In Sensibar et al., Cancer Research 55: 2431-2437, 1995, the authors reported on LNCaP cells transfected with a gene encoding clusterin, and watched to see if expression of this protein altered the effects of tumor necrosis factor α (TNFα), to which LNCaP cells are very sensitive. Treatment of the transfected LNCaP cells with TNFα was shown to result in a transient increase in clusterin levels for a period of a few hours, but these levels had dissipated by the time DNA fragmentation preceding cell death was observed.

Clusterin is expressed in a number of tumour types including breast (Redondo, M.; Villar, E.; Torres-Munoz, J., et al. Am J Pathol (2000) 157(2):393-9), non-small cell lung carcinoma (July, L. V.; Beraldi, E.; So, A. et al. Mol Cancer Ther (2004) 3(3):223-32.), prostate (Miyake, H.; Nelson, C.: Rennie, P. S.; et al. Cancer Res. (2000) 60(1):170-6), ovarian (Hough, C. D.; Cho, K. R.; Zonderman A. B. et al. Cancer Res. (2001) 61(10):3869-76), renal, and bladder (Miyake, H.; Gleave, M.; Kamidono, S.; Urology (2002) 59(1): 150-4).

Transfection studies in vivo result in the development of a phenotype that is resistant to standard therapies. Inhibition studies result in delay in progression and the promotion of apoptosis, as well as in increased chemotherapy and radiation therapy sensitivity.

Antisense treatment of cancer is still a relatively new science. Certain aspects such as optimal dosing and route of administration are still a matter of study (Gewirtz, A. M. Curr Opin Mol Ther. (1999) 1(3):297-306; and Dean, N. M.; Bennett, C. F.; Oncogene (2003) 22(56):9087-96). Continuous infusion is a requirement of the first generation of antisense therapeutics, which are characterized by rapid clearance from plasma and do not show significant pooling in target tissue. The antisense therapeutics thus administered may not accumulate in target tissues sufficiently to down-regulate the genetic and/protein targets, particularly in solid tumours.

There is a need for therapies that have better tissue pharmacokinetics so that less frequent and inconvenient administration is required. Also, efficient delivery will reduce the risk of unwanted side effects and potential toxicities. Effective systemic therapies must therefore have excellent biodistribution to tumour sites, lymph nodes, and other common sites of metastases, to afford optimal treatment.

PCT Publication WO 00/049937 and PCT Publication WO 03/072591, which are incorporated herein by reference, describe the use of antisense therapy which reduces the expression of clusterin in certain cancers.

SUMMARY OF THE INVENTION

In accordance with the present invention, it has now been determined that effective antisense therapy which achieves biodistribution to tumour tissue and tissues involved in metastasis (lymph nodes) and reduces the expression of clusterin with no increase in toxicity is achieved by administration of 40 to 640 mg, more preferably 300 to 640 mg clusterin antisense oligonucleotide to a patient in need of treatment for a cancer expressing clusterin. In particular, such antisense therapy can be applied in treatment of prostate cancer, lung cancer, renal cancer, bladder cancer, breast cancer, and cancers metastasizing through lymph nodes.

In accordance with one aspect of the invention, there is provided a method for treating cancer using clusterin antisense.

In accordance with another aspect of the invention, there is provided a method for providing antisense therapy which reduces the expression of clusterin to provide therapeutic benefits in the treatment of cancer including administering from 40 to 640 mg anti-clusterin antisense oligonucleotide to a patient in need of treatment for a cancer expressing clusterin.

The amount of anti-clusterin antisense oligonucleotide administered is preferably from 300 to 640 mg.

The anti-clusterin antisense oligonucleotide may have a sequence selected from among Seq. Id. Nos. 1-14, for example CAGCAGCAGAGTCTTCATCAT (SEQ ID No.: 1); ATTGTCTGAGACCGTCTGGTC (Seq. ID No.: 2); or GCTGGGCGGAGTTGGGGGCCT (Seq. ID No.: 3). The amount of anti-clusterin antisense oligonucleotide administered may be from 40 to 640 mg, or 300-640 mg. Administration of the anti-clusterin antisense oligonucleotide may be once in a seven day period, 3 times a week, or more specifically on days 1, 3 and 5, or 3, 5 and 7 of a seven day period of a treatment cycle.

The cancer being treated may be prostate cancer, bladder cancer, ovarian cancer, lung cancer, renal cancer, melanoma, and pancreatic cancer. The patient being treated may suffer from metastases or lymph node involvement. The lung cancer may be non-small cell lung cancer (NSCLC).

The method may further include the administration of a chemotherapeutic agent or agents, and the anti-clusterin antisense oligodeoxynucleotide may be administered before, after or during the chemotherapeutic agent or agents. The chemotherapeutic agents may be cisplatin and gemcitabine, taxotere, and/or paclitaxel.

The method may further include the administration of radiation therapy, instead of or along with chemotherapy. The anti-clusterin antisense oligonucleotide may be administered before, after or during the administration of radiation therapy.

The method may further include the administration of hormone ablation therapy, and the anti-clusterin antisense oligonucleotide may be administered before, after or during the hormone ablation therapy.

The method may include the anti-clusterin antisense oligonucleotide being administered in combination with hormone ablation therapy and chemotherapy.

According to another aspect of the invention, there is provided an antisense-containing pharmaceutical composition packaged in dosage unit form, said pharmaceutical composition including anti-clusterin antisense oligonucleotide, wherein the amount of anti-clusterin antisense oligonucleotide in each dosage unit is from 40 to 640 mg, or 300 to 640 mg. The antisense-containing pharmaceutical composition may have a sequence selected from among Seq. ID Nos. 1-12, and may be an injectable solution or suspension, which may further contain sodium ions.

According to another aspect of the invention, there is provided the use of an anti-clusterin antisense in the manufacture of a medicament for the treatment of cancer, wherein the medicament is formulated to deliver a dosage of 40 to 640 mg, or 300-640 mg, of the antisense to a patient. The antisense may have a sequence selected from among Seq. ID Nos. 1-12.

The medicament may contain sodium ions, and/or be in the form of an injectable solution.

The methods and pharmaceutical compositions of the invention surprisingly result in a lower than expected concentration of clusterin antisense provided to a human to achieve target tissue concentrations. Further, the methods and compositions of the invention result in surprisingly high reduction of clusterin mRNA and clusterin protein in cancer tissue in cancer patients relative to untreated patients. In particular, such extensive down-regulation was unexpected given the requirement to penetrate the blood/prostate barrier.

In accordance with another aspect of the invention, there is provided the use of clusterin antisense for the manufacture of a medicament for the treatment of cancer.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention.

DETAILED DESCRIPTION OF THE INVENTION

Figure 1:
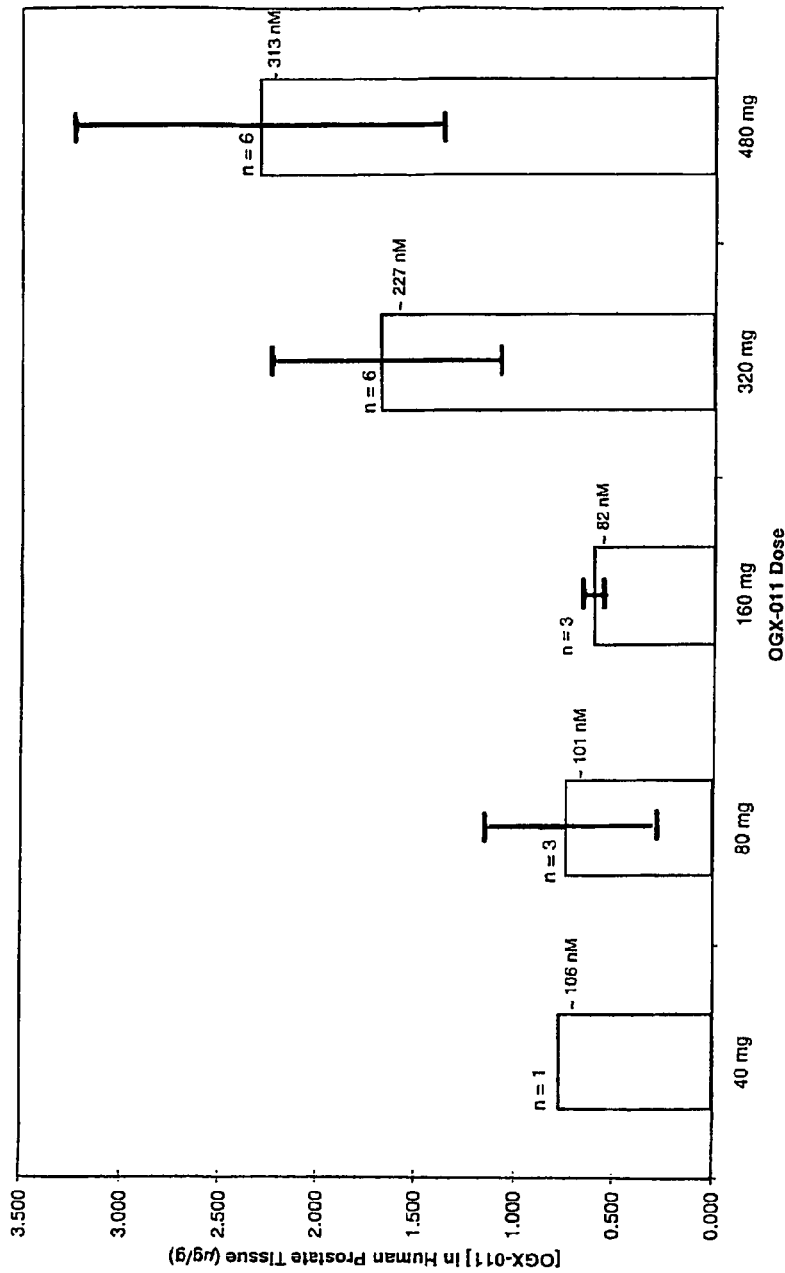
FIG. 1 shows concentrations of anti-clusterin antisense (Seq. ID. No 1) in human prostate tissue (Tissue PK) graphically represented for doses of 40 mg, 80 mg, 160 mg, 320 mg and 480 mg.
Figure 2:
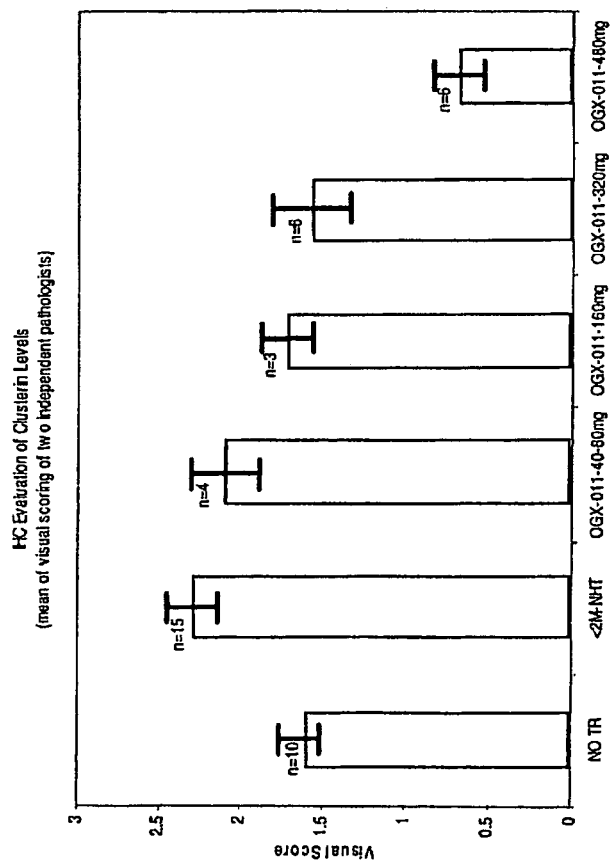
FIG. 2 is a graphical representation of dose dependent decreases in prostate tumour clusterin expression measured by immunohistochemistry (IHC) and in situ hybridization.
Figure 3:
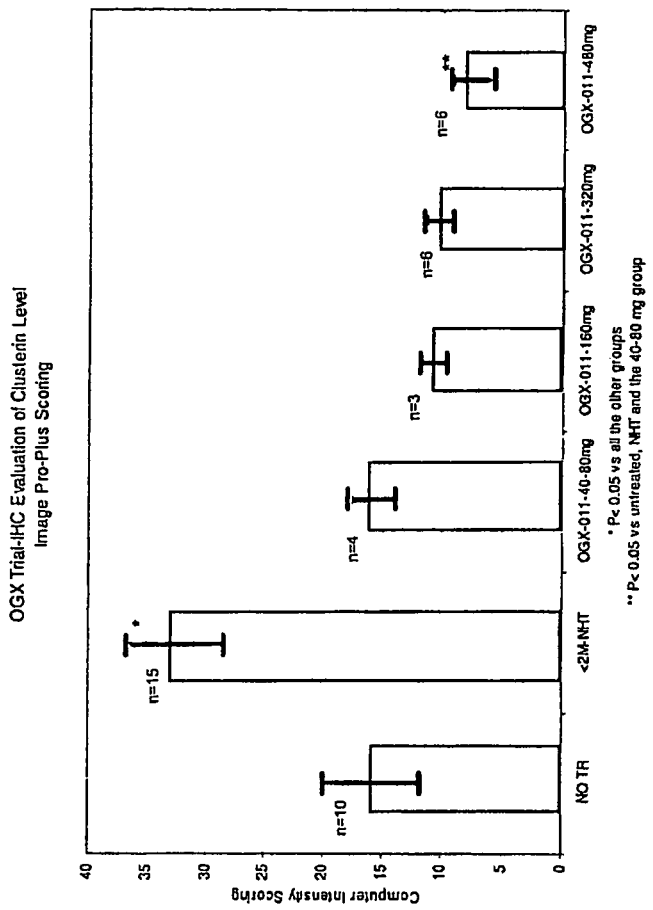
FIG. 3 is a graphical representation showing IHC and computer scoring (Image Pro-Plus™) of all doses as compared to <2 month neoadjuvant hormone therapy and patients receiving no treatment.
Figure 4:
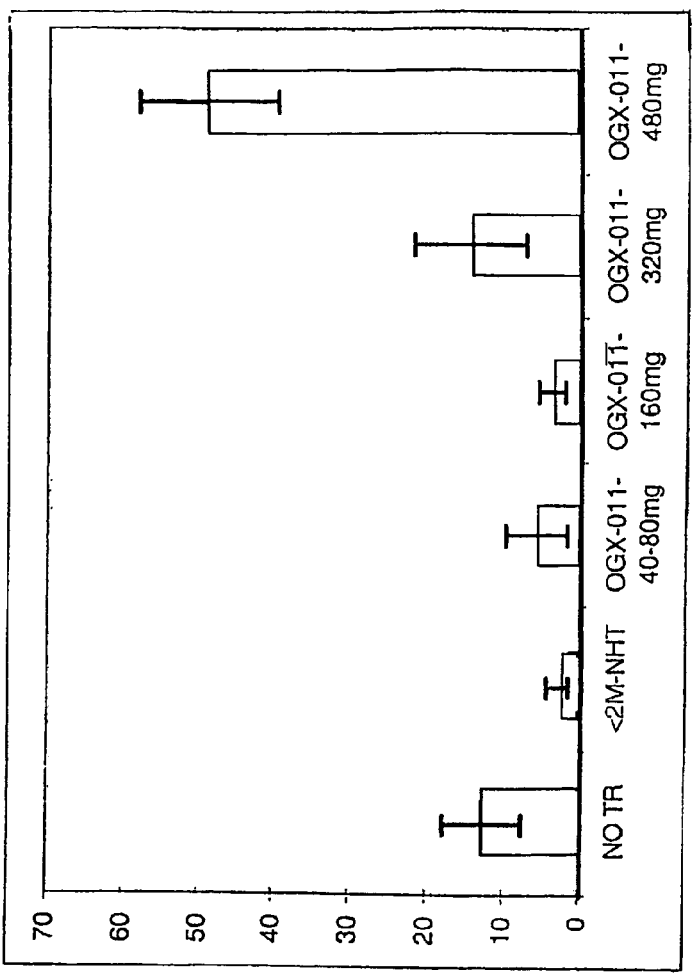
FIG. 4 is a graphical representation showing the clusterin staining intensity of untreated prostate cancer patient cells.
Figure 5:
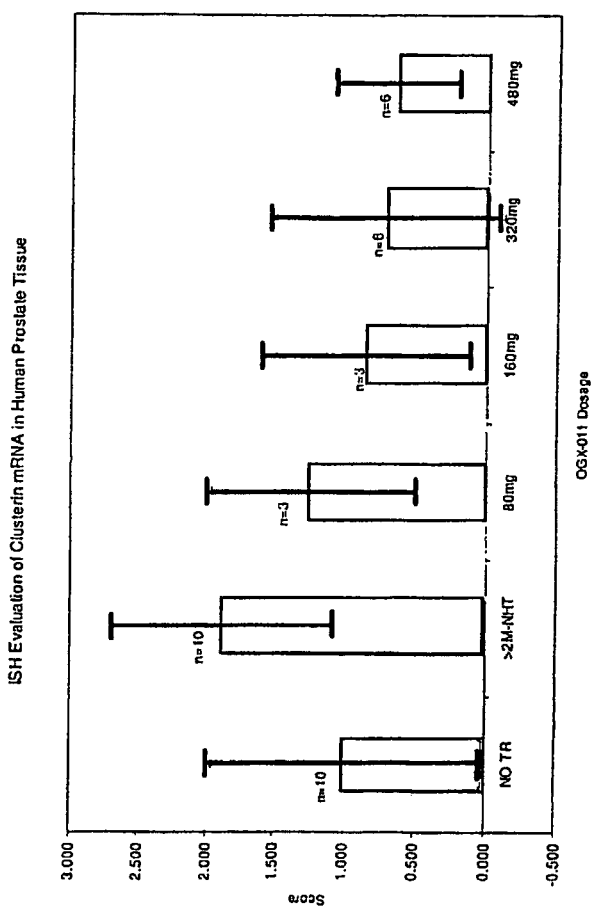
FIG. 5 is a graphical representation showing dose dependent decreases in prostate tumour clusterin mRNA expression as observed by in situ hybridization (ISH), as compared to mRNA expression in patients having <2 month neoadjuvant hormone therapy.
Figure 6:
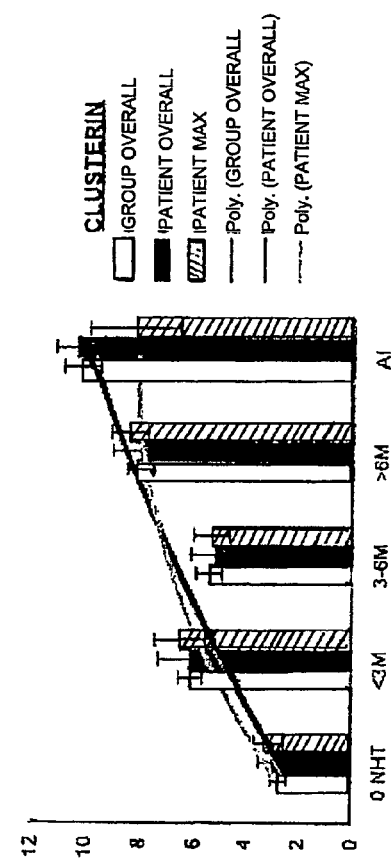
FIG. 6 is a graphical representation showing clusterin staining intensity of untreated prostate cancer patient cells.
Figure 7:
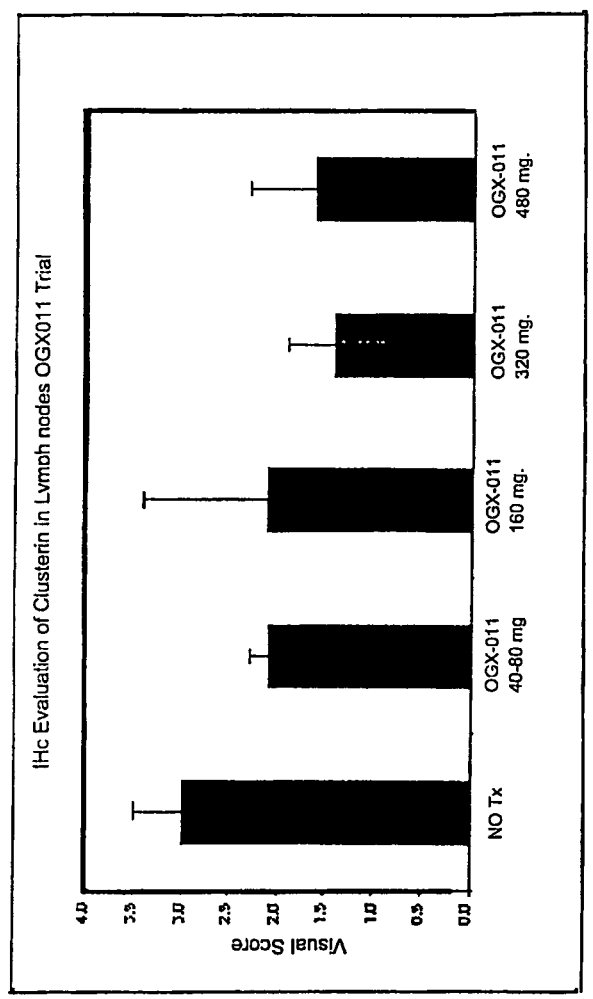
FIG. 7 is a graphical representation showing suppression of clusterin protein expression in lymph nodes.
Figure 8:
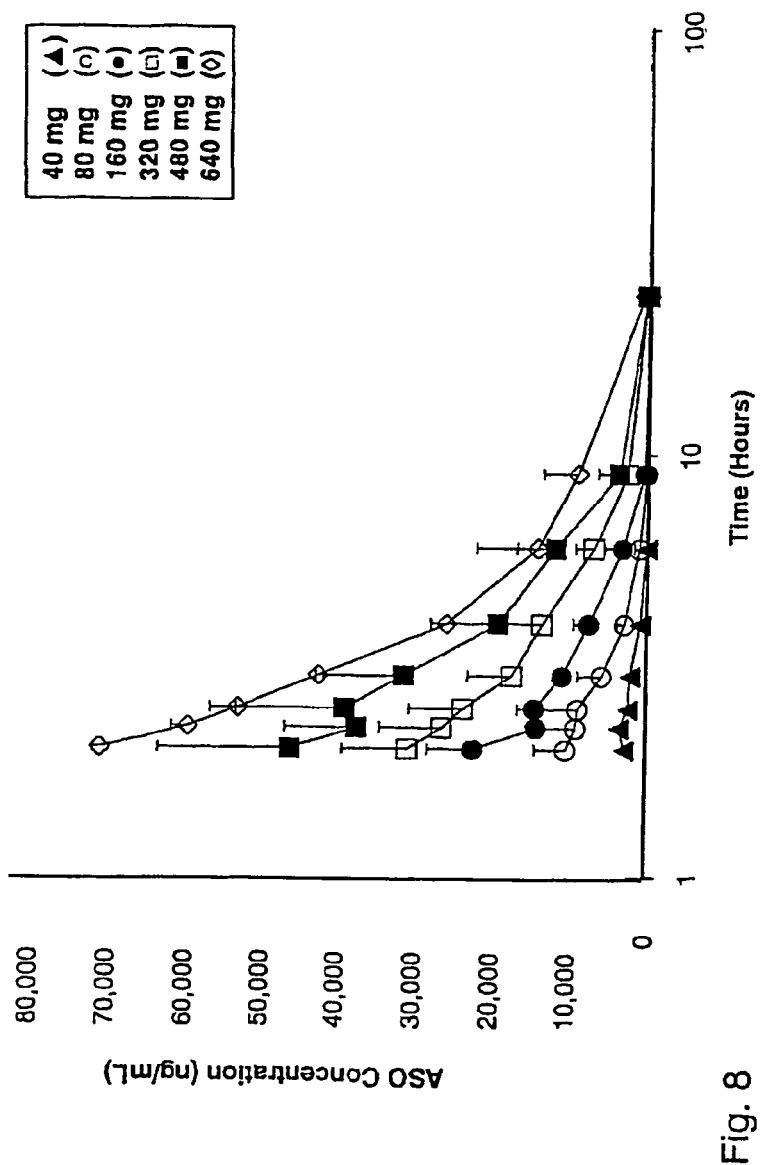
FIG. 8 is a graphical representation of the plasma pharmacokinetics resulting from a single 2 hour intravenous administration.

Numerical values in the specification and claims of this application should be understood to include numerical values which are the same when reduced to the same number of significant figures and numerical values which differ from the stated value by less than the experimental error of the measurement technique used in the present application to determine the value.

As used in the specification and claims of this application, the term "clusterin" refers to the glycoprotein originally derived from rat testes, and to homologous proteins derived from other mammalian species, including humans, whether denominated as clusterin or an alternative name. The sequences of numerous clusterin species are known. For example, the sequence of human clusterin is described by Wong et al., Eur. J. Biochem. 221 (3), 917-925 (1994), and in NCBI sequence accession number NM_001831. In this sequence, the coding sequence spans bases 48 to 1397.

Systematic administration of antisense clusterin oligodeoxynucleotide (ODN or ASO) in animals (including humans) bearing human prostate cancer, lung cancer such as non-small cell lung cancer (NSCLC), bladder cancer, melanoma, breast cancer, renal cancer, ovarian cancer, etc. is effective for inducing apoptosis and delaying disease progression. Systemic administration of antisense clusterin ODN is also effective in delaying progression to androgen independence. Thus, an individual suffering from a clusterin expressing tumour can be treated with chemotherapy, radiation therapy, and in case of hormone-regulated tumours, by initiating androgen-withdrawal to induce apoptotic cell death of tumour cells in the individual, and administering to the individual a composition effective to inhibit expression of clusterin by the tumor cells, thereby promoting apoptosis and/or delaying the progression of tumor cells. Furthermore, combined use of antisense clusterin plus cytotoxic or other chemotherapy (e.g. taxanes) synergistically enhances chemosensitivity in hormone refractory prostate cancer, lung cancers such as NSCLC, breast, ovarian, renal, etc.

Thus, one embodiment of the invention may further include administration of chemotherapy agents or other agents useful in cancer therapy prior to, concurrent with, or subsequent to and/or additional antisense ODNs directed at different targets in combination. For example, the antisense may be administered in conjunction with radiotherapy, surgery, hormone therapy, or chemotherapy.

Further administration may be of hormone ablating agents, or hormone blocking agents. Such agents may be administered in combination with a chemotherapeutic agent to achieve treatment goals.

A second antisense ODN which inhibits expression of an anti-apoptotic protein other than clusterin may also be administered along with the antisense clusterin ODN. For example, antisense clusterin ODN may be used in combination antisense inhibitors to bcl family members or XIAP family members.

An antisense clusterin ODN can also be combined with more conventional chemotherapy agents such as taxanes (Paclitaxel™ or Docetaxel™), mitoxanthrone, gemcitabine, cyclophosphamide, decarbazine, topoisomerase inhibitors, platinum-based chemotherapies such as cisplatin, mitoxanthrone, angiogenesis inhibitors, differentiation agents, signal transduction inhibitors, and ancillary agents in general (such as, but not limited to, Flutamide™).

More than one chemotherapeutic agent may be used in combination with antisense clusterin oligodeoxynucleotide, for example cisplatin/gemcitabine, cisplatin/paclitaxel, cisplatin/docetaxel, or carboplatin/paclitaxel combinations as described in Schiller et al;, N. Eng. J. Med. 346: 92-98 (2002), or a carboplatin/gemcitabine combination.

"Combination" means either at the same time and frequency, or more usually, at different times and frequencies, as the ODN, as part of a single treatment plan. A chemotherapeutic agent will be administered according to the best practice known in the art, specific to that agent. For example, in one aspect, a course of treatment was composed of injections of antisense clusterin oligodeoxynucleotide (for example OGX-011 as defined below) administered over 2 hours on Days 1, 3, 5, 8, 15, 22, and 29; flutamide is administered for 4 weeks daily at 250 mg orally tid beginning on Day 1 to prevent tumour flare, and a single injection of beserelin acetate at 6.3 mg is administered subcutaneously on Day 1. In another aspect, clusterin antisense such as OGX-011 may be given as a 2 hr intravenous (IV) infusion at fixed doses starting at 480 mg weekly after 3 loading doses on days 3, 5, and 7. Cisplatin may be given at 75 mg/m2 IV on day 1, and gemcitabine at 1250 mg/m2 IV on days 1 and 8, for a maximum of 6 21-day cycles. In another schedule, clusterin antisense such as OGX-011 may be given by 2 hr IV infusion at fixed doses starting at 40 mg weekly after loading on days 1, 3, and 5. Taxotere may be given at a standard dose, namely IV 30 mg/m$^2$/week (w) for 5 out of 6 weeks or 75 mg/m$^2$ every 3 weeks.

Chemotherapeutic agents may therefore be used in combination with the antisense clusterin oligodeoxy nucleotide (ODN) according to an aspect of the invention, but yet be administered at different times, different dosages, and at a different frequency, than the ODN is administered.

In other embodiments of the invention, a therapeutic antibody targeted to the particular cancer being treated may be used with the anti-clusterin antisense. One example is for example trastuzumab for breast cancer.

It has also been found that antisense clusterin has beneficial effects for other cancer types. Specifically, antisense clusterin ODN enhances chemosensitivity in human renal cell cancer, a normally chemoresistant disease with no active chemotherapeutic agent having an objective response rate higher than 10%. Radiation sensitivity is also enhanced when cells expressing clusterin are treated with antisense clusterin ODN. Thus, the antisense clusterin ODNs can be used to treat a variety of cancer types in which expression of clusterin has been observed.

Antisense oligonucleotides useful in the present invention are species of oligonucleotide that interact with mRNA encoding clusterin in such a way as to reduce the effective amount of clusterin in the cell. As used in this application, the "effective amount of clusterin" is the amount of clusterin which is present in a form which is functional to provide anti-apoptotic protection. The effective amount of clusterin is reduced by the application of an antisense oligonucleotide complementary to the mRNA encoding clusterin, without regard for the specific mechanism by which the reduction is achieved. Specific antisense species that are useful for this purpose include CAGCAGCAGAGTCTTCATCAT (Seq. ID No. 1), ATTGTCTGAGACCGTCTGGTC (Seq. ID No.: 2), and GCTGGGCGGAGTTGGGGGCCT (Seq. ID No.: 3). A preferred antisense oligonucleotide the 21mer oligonucleotide CAGCAGCAGAGTCTTCATCAT (Seq. ID No.: 1) which is targeted to the translation initiation codon and next 6 codons of the human clusterin sequence (Genbank accession no: NM_001831). Most preferably, this antisense oligonucleotide is used in the form of a 2'-MOE modified clusterin antisense oligonucleotide as described in U.S. patent application Ser. No. 10/080,794 filed Feb. 22, 2002. This oligonucleotide, which is referred to herein as OGX-011, has a phosphorothioate backbone throughout. The sugar moieties of nucleotides 1-4 and 18-21 (the "wings") bear 2'-O-methoxyethyl modifications and the remaining nucleotides (nucleotides 5-17; the "deoxy gap") are 2'-deoxynucleotides. Cytosines in the wings (i.e., nucleotides 1, 4 and 19) are 5-methylcytosines. Other antisense oligonucleotides that may be used in the present invention are those listed in Nos. 4 to 12 below, and those described in U.S. Pat. No. 6,383,808, which is incorporated herein by reference.

| | |
|---|---|
| gcacagcagg agaatcttca t 21 | Seq. ID No. 4 |
| gcacagcagc aggatcttca t 21 | Seq. ID No. 5 |
| tggagtctt gcacgcctcg g 21 | Seq. ID No. 6 |
| ccttcagctt tgtctctgat t 21 | Seq. ID No. 7 |
| agcagggagt cgatgcggtc a 21 | Seq. ID No. 8 |
| atcaagctgc ggacgatgcg g 21 | Seq. ID NO. 9 |
| gcaggcagcc cgtggagttg t 21 | Seq. ID No. 10 |
| ttcagctgct ccagcaagga g 21 | Seq. ID No. 11 |
| aatttagggt tcttcctgga g 21 | Seq. ID No. 12 |

Phase I pharmacokinetic and pharmacodynamic studies conducted with this 2'-MOE modified oligonucleotide in patients with prostate cancer prior to radical prostatectomy show that the biodistribution and down-regulated in vivo is achieved at lower concentrations than predicted from in vitro and in vivo tests, allowing broader range and decreased frequency of dosing of the therapeutic agent. Thus, in accordance with the invention, there is provided a method for providing antisense therapy which reduces the expression of cluster in the treatment of cancer including the step of administering from 40 to 640 mg clusterin antisense oligonucleotide to a patient in need of treatment for a cancer expressing Clusterin, more preferably from 300 to 640 mg. Dosages are calculated typically by patient weight, and therefore a dose range of about 1-20 mg/kg, or about 2-10 mg/kg, or about 3-7 mg/kg, or about 3-4 mg/kg could be used. This dosage is repeated at intervals as needed, clinical concept is dosing once per week with 3 loading doses during week one of cycle one only. The amount of antisense ODN administered is one that has been demonstrated to be effective in human patients to inhibit the expression of clusterin in cancer cells.

The invention further provides antisense containing pharmaceutical compositions packaged in dosage unit form, wherein the amount in each dosage unit is from 40 to 640 mg of the clusterin antisense oligonucleotide, more preferably from 300 to 640 mg. Dosage units may be, without limitation, injectable solutions or suspensions including solutions in bags for IV administration through an existing port, catheter or IV site, and powders or concentrates for preparation of injectable solutions. A formulation of particular usefulness is one including sodium salts in an aqueous solution, for use in intravenous, subcutaneous, intraperitoneal, or intratumour administration.

The invention will now be further described with reference to the following, non-limiting examples.

Example 1

Enhancing Hormone Sensitivity Using Various Clusterin ASOs in Murine Model

Targeting cell survival genes up-regulated by androgen withdrawal may enhance castration-induced apoptosis and thereby prolong time to overt recurrence. ASOs corresponding to the clusterin translation initiation site were designed and shown to reduce clusterin levels in a dose-dependent and sequence-specific manner (Miyake, H.; Nelson, C.; Rennie, P. S. et al. Cancer Res. (2000) 60(1):170-6; Miyake, H.; Chi, K.; Gleave, M. E. Clinical Cancer Res (2000) 6:1655-63).

Male mice bearing Shionogi tumours were castrated 2 to 3 weeks after tumour implantation, at which time tumours were 1 to 2 cm in diameter, and randomly selected for treatment with antisense clusterin versus mismatch control oligonucleotides. Beginning 1 day after castration, 12.5 mg/kg of oligonucleotide was administered once daily by intraperitoneal injection for 40 days. Shionogi tumours regressed faster and complete regression occurred earlier in mice treated with clusterin ASO compared to controls. Furthermore, clusterin ASO treatment significantly delayed recurrence of AI tumours compared to mismatch control oligonucleotide treatment. After an observation period of 50 days post-castration, mean tumour volume in the mismatch-treated control group was 6-times that of the ASO-treated group. Dose-dependent studies using mouse clusterin ASOs in the murine Shionogi model demonstrated dose-dependent activity up to 25 mg/kg/day, but did not reveal any obvious toxicity in mice treated with up to 50 mg/kg/day. Analysis of tumours excised 3 days after castration confirmed that ASO treated tumours had lower clusterin levels and earlier evidence of PARP cleavage fragments, consistent with earlier onset of castration-induced apoptosis. Changes in clusterin mRNA levels in various normal mouse organs after ASO treatment were also evaluated. Shionogi tumours, spleen, kidney, brain and prostate were harvested 3 days post-castration for RNA extraction from mouse administered ASO or mismatch control under the same treatment schedule described above.

Murine clusterin ASO had no effect on clusterin expression levels in spleen, kidney and brain, whereas clusterin mRNA expression in tumour and prostate tissues was significantly lower after ASO administration compared to mismatch control (Miyake H (a), 2000).

Example 2

Characterization of Human Clusterin ASO-OGX-011

ASO sequences directed against different sites on the human clusterin gene were synthesized and tested for their ability to decrease clusterin gene expression in human prostate cancer cell lines that overexpress clusterin (PC3 and LNCaP). The clusterin gene was 'walked' using a quantitative TaqMan RT-PCR assay, which compared the potency of over 80 clusterin ASOs. An active and novel 21-mer ASO (5'-CAGCAGCAGAGTCTTCATCAT-3'; SEQ ID NO. 1), complementary to the translation initiation site of human clusterin, was capable of inhibiting clusterin mRNA expression by up to 90%. OGX-011 has this optimal sequence, and is a 2nd-generation ASO using a phosphorothioate backbone and an additional 2'-O-(2-methoxy) ethyl (2'-MOE) modification to the 2'-position of the carbohydrate moiety on the 4 nucleotides at the 5' and 3' ends of the molecule (gapmer).

Example 3

Enhancing Chemotherapy Sensitivity Using Clusterin ASOs in Prostate Cancer

Clusterin ASOs also increased the cytotoxic effects of mitoxantrone and paclitaxel, reducing the IC50 of PC3 and Shionogi cells by 75%-90% (Miyake, H.; Rennie, P.; Nelson C. et al. (2000) Cancer Res 60:2547-54; and Miyake, H.; Chi, K.; Gleave, M. E. (2000) Clinical Cancer Res 6:1655-63). Cytotoxicity of 10-nM paclitaxel increased in a dose-dependent manner as the concentration of clusterin ASO increased. The induction of apoptosis by 10-nM paclitaxel, as demonstrated by DNA laddering and PARP cleavage, could only be seen when used with clusterin ASOs.

Synergy between clusterin ASOs and chemotherapy also occurs in vivo. The recurrence of AI Shionogi tumours is delayed longest with combined clusterin ASOs and paclitaxel compared to either agent alone. Although clusterin ASOs had no effect on the growth of established AI Shionogi or PC3 tumours, clusterin ASOs synergistically enhanced paclitaxel-induced tumour regression in both the Shionogi and human PC3 models (Miyake, H. 2000; Miyake, H, 2000, as above).

Example 4

Enhancing Chemotherapy Sensitivity Using Clusterin ASOs in Renal Cancer

Clusterin may also play a role in mediating chemoresistance in renal cell carcinoma and other tumours. ASO decreased clusterin levels in human renal cell cancer Caki-2 cells in a dose-dependent and sequence-specific manner. Pretreatment of Caki-2 cells with these clusterin ASO's significantly enhanced chemosensitivity to paclitaxel in vitro. Characteristic apoptotic DNA-laddering occurred after combined treatment with OGX-011 plus paclitaxel, but not with either agent alone. In vivo administration of OGX-011 enhanced in a synergistic fashion paclitaxel-induced Caki-2 tumour regression and delayed tumour progression by 50%.

Example 5

Enhancing Radiation-Sensitivity Using Human Clusterin ASOs In Vitro

Clusterin-overexpressing LNCaP cells were less sensitive to irradiation with significantly lower cell-death rates (23% after 8 Gy) compared to parental LNCaP cells (50% after 8 Gy) 3 days after irradiation (Zellweger, T.; Chi, K.; Miyake, H.; et al. Clin Cancer Res. (2002) 8(10):3276-84). Clusterin expression in PC-3 cells after radiation increased in a dose-dependent manner in vitro by 70% up to 12 Gy and in vivo by >80%. Inhibition of clusterin expression in PC-3 cells using clusterin ASO's before radiation significantly decreased PC-3 cell growth rate and plating efficiency, and enhanced radiation-induced apoptosis. In vivo administration of clusterin ASO before and after radiation significantly reduced PC-3 tumour volume by 50% at 9 weeks as compared to mismatch control oligonucleotides.

These findings support the hypothesis that clusterin acts as a cell survival protein that mediates radioresistance through the inhibition of apoptosis.

Example 6

OGX-011 Pre-Clinical Data

As a class, the second-generation phosphorothioate 2'-O-methoxyethyl ribose gapmer antisense oligonucleotides have pharmacokinetic and toxicity profiles favorable for the intended clinical use. Pharmacokinetics of these compounds are characterized by rapid clearance from plasma following intravenous administration and broad distribution to tissues. Once distributed to tissues, these second generation ASO are cleared slowly. Tumour concentrations of an unmodified (first generation) phosphorothioate clusterin ASO corresponding to SEQ ID NO. 4 was compared to OGX-011. Using the PC3 model, animals were treated with ASO, tumours excised 24, 72, 120 and 168 hours after last dosing and tumour ASO concentration assessed by capillary gel electrophoresis. At 24 hours, OGX-011 concentration was ten times greater than that of unmodified ASO (755+261 nM vs 60+10 nM). In addition, only 10% of the unmodified phosphorothioate ASO were full length while 90% of the OGX-011 ASO detected in the tumours were full length. At 120 hours after the last treatment, the phosphorothioate ASO were not detectable, however OGX-011 remained detectable at 120 hours (632+192 nM) and 168 hours (180+14.1 nM) and also was predominantly full length (approximately 90% of detected ASO) (Zellweger, T.; Miyake, H.; Cooper, S.; et al. J Pharmacol Exp Ther (2001) 298:934-40).

In animal toxicology and pharmacokinetic studies, OGX-011 was administered by I.V. injection at doses of 1, 5, 20 and 50 mg/kg to CD-1 mice, and 1-hour I.V. infusion at 1, 3, and 10 mg/kg to rhesus monkeys. In both species, the dosing period was 4 weeks with alternate day dosing for the first 4 doses (a "loading period") and weekly thereafter (a "maintenance period"). This dosing regimen was based on existing knowledge about the long tissue half-lives of this class of compound.

No clinical signs of toxicity were observed after 4 weeks of exposure at doses up to 50 mg/kg in mice or 10 mg/kg in monkeys. Despite similar levels of tissue exposure in liver achieved in monkeys, mice were generally more sensitive to liver toxicities as indicated by elevated transaminases. Many of the toxicities observed in mice were thought to be related to a generalized mild immunostimulation, an effect of phosphorothioate oligonucleotides that is generally more prominent in rodents than in primates (Parker S L. Cancer Statistics 65: 5-27, 1996).

Genetic toxicity studies (in vitro bacterial cell gene mutation and mouse lymphoma gene mutation) were negative.

Example 7

Changes in Clusterin Expression in Human Prostate Cancer Specimens after Neoadjuvant Hormone Therapy (NHT)

Materials:
Buserelin acetate (Aventis). Each implant dose, in the form of two cream-filled rods, contains a total of 6.6 mg buserelin acetate (6.3 mg base) and 26.4 poly-(D,L-lactide-co-glycolide) in a 75:25 molar ratio. Both rods are implanted in one operation into the subcutaneous tissue of the lateral abdominal wall.

Flutamide is an approved commercially available non-steroidal agent that specifically blocks androgen-binding receptors.

Methods and Results:
To define temporal changes in clusterin in human prostate cancer, 128 radical prostatectomy specimens from patients after 0, 3 or 8 months of NHT were stained for clusterin using immunohistochemistry (July L V, Akbari M, Zellweger T, et al. Prostate 50: 179-188, 2002). Residual foci of cancer cells from radical prostatectomy specimens treated with NHT exhibited strongly positive staining (intensity+3, +4) for clusterin in 80-90% of the surviving cancer cells compared to either absent (0) or low intensity staining (+1 to +2) in 10-20% of cancer cells in non-NHT treated specimens. Consistent with previous reports, staining for clusterin was found in the cytoplasm of luminal epithelial cells, and no nuclear staining was observed.

Western blot analyses of clusterin were performed on prostate cancer specimens from untreated patients (n=5), NHT treated patients (n=5) and two patients with androgen independent disease. To compare changes in protein expression, a normalization procedure against the cytokeratin to vimentin ratio was performed because of increases in the stromal to epithelial ratio that occur with NHT. Normalized clusterin levels were significantly higher in all treated patients compared with untreated patients, increasing 17-fold after androgen ablation. These data confirm that clusterin increases in prostate cancer cells after immediately following androgen withdrawal and support the hypothesis that clusterin serves as a protective against the apoptotic stimulus of androgen ablation.

Example 8

Safety, Plasma and Tissue Pharmacokinetics, and Tissue Pharmacodynamics of OGX-011 in Prostate Cancer Patients Materials
Phosphorothioate 2'-O-methoxyethyl ribose ASO targeted to the translation initiation site of clusterin mRNA (designated OGX-011), is formulated as OGX-011 Injection, 20 mg/mL, in an isotonic, phosphate-buffered saline solution (pH 7.4) for intravenous (I.V.) administration; the drug product solution may be diluted into saline prior to I.V. administration. The formulation details are listed in Table 1.

Buserelin acetate (Aventis)—see above.
Flutamide—see above.

TABLE 1

| Ingredients | Concentration |
| --- | --- |
| OGX-011 | 20 mg/mL |
| Dibasic sodium phosphate, heptahydrate, USP | 14.33 mg/mL |
| Monobasic sodium phosphate, monohydrate, USP | 1.73 mg/mL |
| Sodium chloride, USP | 2.70 mg/mL |
| Hydrochloric Acid, NF | pH adjustment |
| Sodium Hydroxide, NF | pH adjustment |
| Water for Injection, USP | q.s. to 1.0 mL |

Methods:
Patients having localized prostate cancer with high-risk features and candidates for prostatectomy were enrolled to this dose escalation trial. Twenty patients were treated and evaluated.

Each course of treatment was composed of injections of OGX-011 administered over 2 hours on Days 1, 3, 5, 8, 15, 22, and 29 using fixed dose escalation plan starting at 40 mg; 4 weeks of daily flutamide 250 mg orally tid beginning on Day 1 to prevent tumour flare, and a single injection of beserelin acetate 6.3 mg subcutaneously on Day 1. Each patient received a maximum of 1 course only.

Prostatectomy was performed day 30-36. Prostate tissue concentrations of OGX-011 were determined by a fully validated ELISA method. Briefly, clusterin mRNA in human prostate tissues were determined by in situ hybridization using standardized controls including OGX-011 and human plasma (EDTA) (Biochemed), and reagents including Qiagen cutting Probe 112989 cut (5' end biotinated, 3' end is labeled with digoxigenin), S1 nuclease (Life Technologies), anti-digoxigenen-Fab fragments conjugated with alkaline phosphatase (AP), AttoPhos® fluorescent substrate and AttoPhos® reconstitution buffer, and Reacti-Bind™ NeutrAvidin™ (Pierce) coated Nalgene™ Nunc™ flat-bottomed polystyrene 96-well microwell plates blocked with SuperBlock®. Various label-recommended buffers and salts were also used, purchased from various sources such as Fisher Scientific, Laboratoire MAT, Sigma, VWR, BDH, Pierce, and BioSource. Polypropylene containers were used to prepare and store all reference standard solutions.

Clusterin protein in human prostate tissues was also determined by:
1. IHC using visual scoring of tumour cells conducted by two independent pathologists. Specimens were graded from 0 to +3 intensity, representing the range from no staining to heavy staining and the overall percentage of cancer cells showing staining (0-100%) was indicated. The mean of the two pathologists' scores (the product of intensity and percentage of cells) was used for reporting and standard error reported; and
2. IHC using an automated scoring system of tumour cells conducted by an Image Pro-Plus™ system. The scoring system used by Image Pro™ can be defined by the user to provide greater gradations and provide additional independent semi-quantitative data.

Results:
Toxicity was limited to grade 1 or 2, and included fevers, rigors, fatigue and transient AST and ALT elevations at higher doses of OGX-011. Plasma pharmokinetics analysis showed linear increases in AUC with a t1/2 of approximately 2 hours.

The 40 mg, 80 mg and 160 mg dose cohorts achieved mean concentrations of OGX-011 that were approximately equivalent and thus not dose dependent. OGX-011 concentrations increased to a mean of 1.668 :g/g (~227 nM) at 320 mg and 2.30 :g/g (~313 nM) at 480 mg dosing, representing a 4.9 fold increase and 6.76 fold increase at the 320 mg and 480 mg dose, respectively.

As measured by immunohistochemistry, each of the 320 mg and 480 mg dose cohorts achieved a 30% decrease in clusterin protein expression as compared to <2 month neoadjuvant hormone therapy. The mean percent of down-regulation of clusterin protein in the 320 mg and 480 mg dose cohorts was 31.2% and 70.6%, respectively. The mean percent age of cancer cells in untreated prostate cancer patients staining intensity "0", or no clusterin protein, was 14.25%, and cells staining intensity "3," (high clusterin protein) was 18.75%. Following <2 months of neoadjuvant hormone therapy, the percentage of cancer cells staining intensity 0 decreased to 1.5%, and cells staining intensity 3 increased to 48%. Surprisingly, the mean percentage of cancer cells staining intensity 0, 1, 2 and 3 in prostate cancer patients receiving 320 mg OGX-011 was restored to approximately equivalent levels to untreated controls. The mean percentage of cancer cells staining intensity 0 increased dramatically in patients treated with 480 mg of OGX-011 to 48.17%. In this same dose cohort, the percentage of cancer cells staining intensity 3 decreased dramatically to 6.56%.

IHC and computer scoring (Image Pro-Plus™) of all doses as compared to <2 month neoadjuvant hormone therapy showed a mean percent down regulation of clusterin protein in the 320 mg and 480 mg dose cohorts of 68.7% and 76.8%, respectively.

Example 9

Antisense Oligonucleotide to Clusterin (OGX-011) in Combination with Gemcitabine and Cisplatin As First-Line Treatment For Patients With Advanced Non-Small Cell Lung Cancer (NSCLC)

Patients with previously untreated stage IIIB or IV NSCLC were eligible. OGX-011 was given as a 2 hr IV infusion at fixed doses starting at 480 mg weekly after 3 loading doses on days 7, 5, and 3). Cisplatin was given at 75 mg/m2 IV on day 1, and gemcitabine at 1250 mg/m2 IV on days 1 and 8. A maximum of 6 21-day cycles were performed.

Serum clusterin levels were measured at baseline and on day 1 of each cycle. Where possible, pre- and post-treatment (cycle 2, day 1) biopsies of the tumours were taken. The toxicities observed were typical for cisplatin/gemcitabine therapy alone.

The combination of OGX-011 and cisplatin/gemcitabine is more effective than either treatment alone.

The invention claimed is:

1. A method for providing antisense therapy which reduces the expression of clusterin to provide therapeutic benefit in the treatment of cancer comprising administering from 480 mg to 640 mg anti-clusterin antisense oligonucleotide intravenously to a human in need of treatment for a cancer expressing clusterin, which human also receives hormone ablation therapy, radiation therapy or a chemotherapeutic agent, wherein the nucleotide sequence of the anti-clusterin antisense oligonucleotide is CAGCAGCAGAGTCTTCATCAT (Seq. ID No.: 1), wherein the anti-clusterin antisense oligonucleotide has a phosphorothioate backbone throughout, has sugar moieties of nucleotides 1-4 and 18-21 bearing 2'-O-methoxyethyl modifications, has nucleotides 5-17 which are 2' deoxynucleotides, and has 5-methylcytosines at nucleotides 1, 4, and 19.

2. The method of claim 1, wherein the amount of anti-clusterin antisense oligonucleotide administered is 640 mg.

3. The method of claim 1, wherein the anti-clusterin antisense oligonucleotide is administered once in a seven day period.

4. The method of claim 1, wherein the anti-clusterin antisense oligonucleotide is administered on day 1, 3 and 5 of the first seven day period of a treatment cycle, and once in a seven day period thereafter.

5. The method of claim 1, wherein the cancer is prostate cancer, bladder cancer, ovarian cancer, lung cancer, renal cancer, melanoma, or pancreatic cancer.

6. The method of claim 5, wherein the human suffers from metastases.

7. The method of claim 5, wherein the human suffers from cancer with lymph node involvement.

8. The method of claim 1, wherein the human receives a chemotherapeutic agent.

9. The method of claim 8, wherein the chemotherapeutic agent is gemcitabine.

10. The method of claim 8, wherein the chemotherapeutic agent is carboplatin.

11. The method of claim 8, wherein the chemotherapeutic agent is paclitaxel.

12. The method of claim 8, wherein the chemotherapeutic agent is paclitaxel and carboplatin.

13. The method of claim 8, wherein the chemotherapeutic agent is docetaxel.

14. The method of claim 8, wherein the chemotherapeutic agent is prednisone.

15. The method of claim 8, wherein the chemotherapeutic agent is mitoxantrone.

16. The method of claim 1, wherein the chemotherapeutic agent is mitoxantrone and prednisone.

17. The method of claim 1, wherein the chemotherapeutic agent is docetaxel and prednisone.

18. The method of claim 1, wherein the cancer is non-small cell lung cancer.

19. The method of claim 1, wherein the cancer is prostate cancer.

20. The method of claim 1, wherein the cancer is renal cancer.

21. The method of claim 1, wherein the cancer is breast cancer.

22. The method of claim 12, wherein the cancer is non-small cell lung cancer.

23. The method of claim 22, wherein the amount of anti-clusterin antisense oligonucleotide administered is 640 mg.

24. The method of claim 23, wherein the anti-clusterin antisense oligonucleotide is in an aqueous solution comprising sodium ions.

25. The method of claim 17, wherein the cancer is prostate cancer.

26. The method of claim 25, wherein the amount of anti-clusterin antisense oligonucleotide administered is 640 mg.

27. The method of claim 26, wherein the anti-clusterin antisense oligonucleotide is in an aqueous solution comprising sodium ions.

28. The method of claim 16, wherein the cancer is prostate cancer.

29. The method of claim 28, wherein the amount of anti-clusterin antisense oligonucleotide administered is 640 mg.

30. The method of claim 29, wherein the anti-clusterin antisense oligonucleotide is in an aqueous solution comprising sodium ions.

31. A method for providing antisense therapy which reduces the expression of clusterin to provide therapeutic benefit in the treatment of prostate cancer comprising administering intravenously 640 mg anti-clusterin antisense oligonucleotide in an aqueous solution once in a seven day period to a human in need of treatment for prostate cancer expressing clusterin, which human also receives docetaxel and prednisone, wherein the nucleotide sequence of the anti-clusterin antisense oligonucleotide is CAGCAGCAGAGTCTTCATCAT (Seq. ID No.: 1), wherein the anti-clusterin antisense oligonucleotide has a phosphorothioate backbone throughout, has sugar moieties of nucleotides 1-4 and 18-21 bearing 2'-O-methoxyethyl modifications, has nucleotides 5-17 which are 2'deoxynucleotides, and has 5-methylcytosines at nucleotides 1, 4, and 19.

32. A method for providing antisense therapy which reduces the expression of clusterin to provide therapeutic benefit in the treatment of non-small cell lung cancer comprising administering intravenously 640 mg anti-clusterin antisense oligonucleotide in an aqueous solution once in a seven day period to a human in need of treatment for non-small cell lung cancer expressing clusterin, which human also receives paclitaxel and carboplatin, wherein the nucleotide sequence of the anti-clusterin antisense oligonucleotide is CAGCAGCAGAGTCTTCATCAT (Seq. ID No.: 1), wherein the anti-clusterin antisense oligonucleotide has a phosphorothioate backbone throughout, has sugar moieties of nucleotides 1-4 and 18-21 bearing 2'-O-methoxyethyl modifications, has nucleotides 5-17 which are 2'deoxynucleotides, and has 5-methylcytosines at nucleotides 1, 4, and 19.

* * * * *

UNITED STATES PATENT AND TRADEMARK OFFICE
CERTIFICATE OF CORRECTION

| | | |
|---|---|---|
| PATENT NO. | : 8,710,020 B2 | Page 1 of 1 |
| APPLICATION NO. | : 11/470331 | |
| DATED | : April 29, 2014 | |
| INVENTOR(S) | : Gleave et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1911 days.

Signed and Sealed this
Eleventh Day of August, 2015

Michelle K. Lee
*Director of the United States Patent and Trademark Office*